United States Patent
Bauer

(10) Patent No.: US 9,550,143 B2
(45) Date of Patent: Jan. 24, 2017

(54) METHOD FOR TREATING A HYDROCARBON-RICH GAS MIXTURE CONTAINING MERCURY AND ACID GASES

(71) Applicant: LINDE AKTIENGESELLSCHAFT, München (DE)

(72) Inventor: Heinz Bauer, Ebenhausen (DE)

(73) Assignee: Linde Aktiengesellschaft, Munich (DE)

( * ) Notice: Subject to any disclaimer, the term of this patent is extended or adjusted under 35 U.S.C. 154(b) by 19 days.

(21) Appl. No.: 14/764,238

(22) PCT Filed: Feb. 4, 2014

(86) PCT No.: PCT/EP2014/000299
§ 371 (c)(1),
(2) Date: Jul. 29, 2015

(87) PCT Pub. No.: WO2014/131489
PCT Pub. Date: Sep. 4, 2014

(65) Prior Publication Data
US 2015/0360169 A1 Dec. 17, 2015

(30) Foreign Application Priority Data

Feb. 28, 2013 (DE) .................. 10 2013 003 415

(51) Int. Cl.
*B01D 53/02* (2006.01)
*B01D 53/14* (2006.01)
(Continued)

(52) U.S. Cl.
CPC ....... *B01D 53/1437* (2013.01); *B01D 53/0423* (2013.01); *B01D 53/1456* (2013.01);
(Continued)

(58) Field of Classification Search
CPC ............. C07C 9/04; C07C 7/11; C07C 7/12; B01D 2256/245; B01D 2257/304; B01D 2257/308; B01D 2257/504; B01D 2257/602; B01D 2257/70; B01D 2259/65; B01D 53/0423; B01D 53/1437; B01D 53/1456; C10L 2290/542; C10L 3/101; C10L 3/102; Y02C 10/08; Y02P 20/152

See application file for complete search history.

(56) References Cited

U.S. PATENT DOCUMENTS

| | | | | |
|---|---|---|---|---|
| 5,053,209 A | | 10/1991 | Yan | |
| 5,096,673 A | * | 3/1992 | Gammie | B01D 8/00 422/198 |
| 5,141,724 A | * | 8/1992 | Audeh | B01D 53/02 423/210 |
| 5,419,884 A | * | 5/1995 | Weekman | B01D 53/02 208/253 |
| 5,989,506 A | * | 11/1999 | Markovs | B01D 53/04 208/251 R |
| 8,790,427 B2 | * | 7/2014 | O'Rear | B01D 53/1493 423/210 |
| 2005/0084976 A1 | * | 4/2005 | Baldwin | G01N 33/0045 436/81 |
| 2008/0210089 A1 | * | 9/2008 | Tsangaris | C10J 3/00 95/90 |
| 2009/0320678 A1 | * | 12/2009 | Chang | B01D 46/002 95/92 |

(Continued)

FOREIGN PATENT DOCUMENTS

EP 0893152 A1 1/1999

*Primary Examiner* — Christopher P Jones
(74) *Attorney, Agent, or Firm* — David A. Hey

(57) ABSTRACT

A method for treating a hydrocarbon-rich gas mixture containing mercury and acid gases, said gas mixture being natural gas in particular, wherein the gas mixture is subject to an adsorptive mercury removal and a downstream acid-gas scrubbing. Before the gas mixture to be treated is fed to the adsorptive mercury removal, the gas mixture to be treated is heated at least to such an extent that the gas mixture does not fall below the water dew point in the adsorptive mercury removal and does not fall below the hydrocarbon dew point in the acid-gas scrubbing.

6 Claims, 1 Drawing Sheet

(51) Int. Cl.
*B01D 53/04* (2006.01)
*C07C 7/11* (2006.01)
*C07C 7/12* (2006.01)
*C10L 3/10* (2006.01)

(52) U.S. Cl.
CPC .................. *C07C 7/11* (2013.01); *C07C 7/12* (2013.01); *C10L 3/101* (2013.01); *C10L 3/102* (2013.01); *B01D 2256/245* (2013.01); *B01D 2257/304* (2013.01); *B01D 2257/308* (2013.01); *B01D 2257/504* (2013.01); *B01D 2257/602* (2013.01); *B01D 2257/70* (2013.01); *B01D 2259/65* (2013.01); *C10L 2290/542* (2013.01); *Y02C 10/08* (2013.01); *Y02P 20/152* (2015.11)

(56) References Cited

U.S. PATENT DOCUMENTS

| | | |
|---|---|---|
| 2012/0000359 A1 | 1/2012 | Bresler et al. |
| 2013/0291722 A1 | 11/2013 | Stallman |
| 2014/0072489 A1* | 3/2014 | O'Rear .............. B01D 53/1493 423/210 |

* cited by examiner

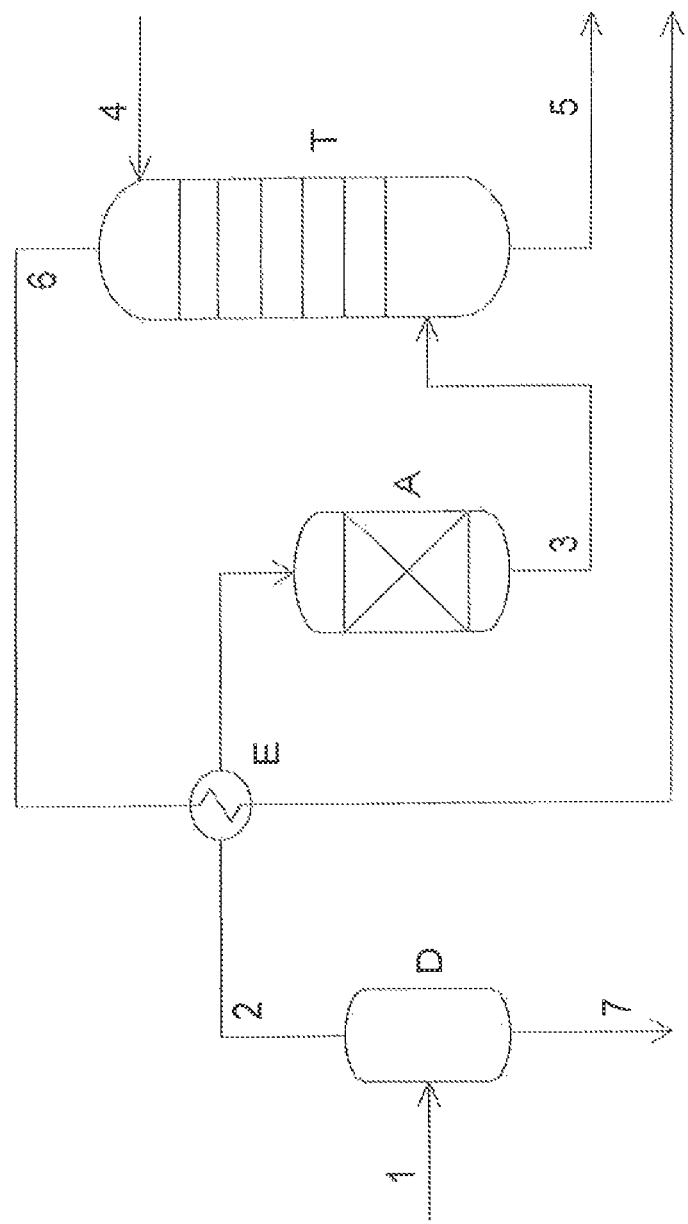

METHOD FOR TREATING A HYDROCARBON-RICH GAS MIXTURE CONTAINING MERCURY AND ACID GASES

The invention relates to a method for treating a mercury- and acid gases-containing hydrocarbon-rich gas mixture, in particular natural gas, wherein said mixture is subjected to an adsorptive mercury removal and a subsequent acid gas scrub.

The removal of mercury from the abovementioned gas mixtures protects plant parts containing aluminum alloys from corrosion and also protects humans and the environment from the toxic effects of mercury and mercury compounds. The proportion of mercury in such gas mixtures is typically between 1 and 1000 $\eta g/Nm^3$. Adsorptive mercury removal processes can reduce this proportion to from 0.01 to 0.001 $\eta g/Nm^3$.

Originally, this could essentially only be achieved with sulfur-impregnated activated carbon which needed to be protected from moisture and was thus installed downstream of the typically provided drying process. The recent use of inorganic support material for the active sulfur compounds makes it possible to use the mercury adsorbers even in the presence of moisture and the adsorptive mercury removal may therefore be implemented upstream or downstream of the acid gas scrub.

The acid gas scrub removes unwanted components, in particular $H_2$, $CO_2$ and COS as typical acidic gas contaminants, in order, inter alia, to prevent plugging and blocking of downstream plant parts. Acid gas scrubs generally contain as scrubbing medium aqueous solutions of chemical compounds which reversibly bind to the acid gases to be removed. Hydrocarbons are only slightly soluble in this type of scrubbing medium.

Arranging the adsorptive mercury removal upstream of the acid gas scrub offers the downstream plant parts the greatest protection against contamination, since in this way neither the acid gas fraction removed by the acid gas scrub nor the regeneration gas required for regenerating the mercury adsorbers contain mercury. Both streams (acid gas traction and regeneration gas) are potentially hazardous to humans and the environment.

The water content of the gas mixture to be treated generally makes it necessary to provide a separator upstream of the adsorptive mercury removal to avoid the downstream mercury adsorber(s) being exposed to liquid. Even when the adsorbent employed does not suffer permanent damage on exposure to liquid, the performance of said adsorbent will be impaired when in a damp state and this could potentially result in incomplete mercury removal.

However it is possible for the temperature of the mixture to fail undesirably, below the dew point for water and/or hydrocarbons during operation of the mercury adsorber, for instance due to entrainment of droplets from the abovmentioned separator or due to the gas mixture cooling down and partially condensing in the line between the separator and the adsorber.

The present invention has for its object the provision of a method of the type in question for treating a mercury- and acid gases-containing hydrocarbon-rich gas mixture, in particular natural gas, where said method guarantees dry operation of a mercury adsorber in the gas phase and precludes unwanted formation of liquid hydrocarbons, and attendant foaming, in the downstream acid gas scrub.

This object is achieved by a method for treating a mercury- and acid gases-containing hydrocarbon-rich gas mixture, characterized in that before being supplied to the adsorptive mercury removal the gas mixture to be treated is warmed at least to an extent sufficient to avoid the temperature thereof falling below the water dew point in the adsorptive mercury removal and falling below the hydrocarbon dew point in the acid gas scrub.

In accordance with the invention the adsorptive mercury removal/the mercury adsorber(s) are controlledly operated at a temperature sufficiently above the dew point to safely prevent the adsorptive mercury removal suffering a loss of performance caused by the presence of liquid. The procedure according to the invention also prevents the unwanted formation of liquid hydrocarbons in the downstream acid gas scrub which would lead to attendant foaming.

In principle, the gas mixture to be treated may be warmed against any desired heat source. The gas mixture to be treated is advantageously warmed against the acid gas-freed fraction withdrawn from the top of the acid gas scrub. This fraction is sufficiently warmed in the acid gas scrub by the heat of binding between the scrubbing medium and the acid gas components and by the introduction of warm scrubbing medium as column reflux.

In a further development of the method according to the invention the gas mixture to be treated is warmed by at least 5° C. to 30° C., preferably by at least 15° C. to 25° C., between exiting the separation process/separator which serves to remove water and entering the acid gas scrub.

The method according to the invention for treating a mercury- and acid gases-containing hydrocarbon-rich gas mixture and advantageous embodiments thereof are more particularly elucidated hereinbelow with reference to the working example shown in FIG. 1.

The damp, mercury- and acid gases-containing hydrocarbon-rich gas mixture 1 is supplied to a separator D in which it is freed of liquid, for example water, said liquid being withdrawn from the separator D via line 7. In accordance with the invention the gas mixture 2 withdrawn at the top of the separator D is warmed in the heat exchanger E at least to an extent sufficient to avoid the temperature thereof falling below the water dew point in the subsequent adsorptive mercury removal A and falling below the hydrocarbon dew point in the acid gas scrub T. In the working example shown in FIG. 1, this warming is accomplished against the acid-gas freed fraction 6 withdrawn from the top of the acid gas scrub T and subsequently supplied, for example, to a complete drying.

The gas mixture 2 warmed in heat exchanger E is freed of mercury in the adsorptive mercury removal to achieve residual mercury contents of from 0.01 to 0.001 $\eta g/Nm^3$. For clarity, the adsorptive mercury removal is shown in the form of an adsorber A. Said adsorber contains an adsorbent/adsorption material suitable for the adsorption of mercury. Said adsorbent/adsorption material requires replacement once exhausted; in-situ regeneration is generally not carried out. Typically, two adsorbers are connected in series. The second adsorber is brought on-line in place of the first as soon as the adsorbent in the first adsorber is exhausted.

The gas mixture 3 withdrawn from the adsorptive mercury removal A and freed of mercury is supplied to the column T which removes the unwanted acid gas components. A suitable scrubbing medium 4 is supplied to the top region of column T. The gas mixture freed of unwanted acid gas components is withdrawn from the top of the column T and sent for further treatment for example a liquefaction, or use.

The invention claimed is:
1. A method for treating a mercury- and acid gases-containing hydrocarbon-rich gas mixture, wherein said mix- ture is subjected to an adsorptive mercury removal, having a separation process connected upstream of it, and a subsequent acid gas scrub, characterized in that between exiting the separation process and being supplied to the adsorptive mercury removal the gas mixture to be treated is warmed at least to an extent sufficient to avoid the temperature thereof falling below the water dew point in the adsorptive mercury removal and falling below the hydrocarbon dew point in the acid gas scrub.

2. The method according to claim 1, characterized in that the gas mixture to be treated is warmed (E) by at least 5° C. to 30° C., between exiting the separation process and entering the acid gas scrub.

3. The method according to claim 1, characterized in that the gas mixture to be treated is warmed against the acid gas-freed fraction withdrawn from the top of the acid gas scrub.

4. The method according to claim 1, characterized in that the proportion of mercury in the gas mixture to be treated is between 1 and 1000 $\eta g/Nm^3$.

5. The method according to claim 1, characterized in that the gas mixture is natural gas.

6. The method according to claim 2, characterized in that the gas mixture to be treated is warmed by at least 15° C. to 25° C.

\* \* \* \* \*